US009849137B2

(12) United States Patent
Henke et al.

(10) Patent No.: US 9,849,137 B2
(45) Date of Patent: Dec. 26, 2017

(54) WATER-SOLUBLE MELOXICAM GRANULES

(71) Applicants: Stefan Henke, Kirchen (DE); Martin A. Folger, Ingelheim (DE); Jens Lehmann, Mandel (DE); Diana C. Keilhofer, Mainz (DE); Hans-Juergen Kroff, Schoeneberg (DE); Nina Herz, Windesheim (DE)

(72) Inventors: Stefan Henke, Kirchen (DE); Martin A. Folger, Ingelheim (DE); Jens Lehmann, Mandel (DE); Diana C. Keilhofer, Mainz (DE); Hans-Juergen Kroff, Schoeneberg (DE); Nina Herz, Windesheim (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 14/444,390

(22) Filed: Jul. 28, 2014

(65) Prior Publication Data

US 2014/0332438 A1 Nov. 13, 2014

Related U.S. Application Data

(60) Division of application No. 13/799,815, filed on Mar. 13, 2013, which is a continuation of application No. 10/694,569, filed on Oct. 27, 2003, now Pat. No. 8,992,980.

(60) Provisional application No. 60/508,184, filed on Oct. 2, 2003.

(30) Foreign Application Priority Data

Oct. 25, 2002 (DE) .................................. 102 50 081

(51) Int. Cl.
| | | |
|---|---|---|
| *A61K 9/51* | (2006.01) | |
| *A61K 31/5415* | (2006.01) | |
| *A61K 9/00* | (2006.01) | |
| *A61K 9/16* | (2006.01) | |
| *A61K 9/50* | (2006.01) | |
| *A61J 1/00* | (2006.01) | |
| *B65D 25/00* | (2006.01) | |

(52) U.S. Cl.
CPC ............ *A61K 31/5415* (2013.01); *A61J 1/00* (2013.01); *A61K 9/0095* (2013.01); *A61K 9/16* (2013.01); *A61K 9/1617* (2013.01); *A61K 9/1635* (2013.01); *A61K 9/1641* (2013.01); *A61K 9/1652* (2013.01); *A61K 9/5078* (2013.01); *A61K 9/5089* (2013.01); *B65D 25/00* (2013.01)

(58) Field of Classification Search
CPC .... A61K 47/26; A61K 9/0056; A61K 9/1623; A61K 9/2077
See application file for complete search history.

(56) References Cited

U.S. PATENT DOCUMENTS

| 4,687,662 A * | 8/1987 | Schobel ............... A61K 9/0007 424/44 |
| 4,702,919 A | 10/1987 | Kitamori et al. |
| 4,802,926 A | 2/1989 | Kussendrager et al. |
| 5,026,560 A * | 6/1991 | Makino ................ A61K 9/1676 424/458 |
| 5,178,878 A | 1/1993 | Wehling et al. |
| 5,283,065 A | 2/1994 | Doyon et al. |
| 5,464,632 A | 11/1995 | Cousin et al. |
| 5,489,439 A | 2/1996 | Bola |
| 5,556,639 A | 9/1996 | Fielden |
| 5,654,003 A | 8/1997 | Fuisz et al. |
| 6,048,557 A * | 4/2000 | Van Den Burg ....... A23C 11/04 426/601 |
| 6,071,539 A | 6/2000 | Robinson et al. |
| 6,077,864 A * | 6/2000 | Burgess et al. ............... 514/468 |
| 6,106,862 A | 8/2000 | Chen et al. |
| 6,183,779 B1 | 2/2001 | Ouali et al. |
| 6,284,269 B1 | 9/2001 | Struengmann et al. |
| 6,550,955 B2 | 4/2003 | D'Silva |
| 6,599,529 B1 | 7/2003 | Skinhøj et al. |
| 6,669,957 B1 | 12/2003 | Laruelle et al. |
| 6,869,948 B1 | 3/2005 | Bock et al. |
| 2002/0006440 A1 | 1/2002 | Cherukuri |
| 2002/0035107 A1 | 3/2002 | Henke et al. |
| 2002/0068088 A1 | 6/2002 | Gruber |
| 2002/0106345 A1 | 8/2002 | Uhrich et al. |
| 2002/0131998 A1* | 9/2002 | Martani ........................ 424/464 |
| 2002/0169212 A1* | 11/2002 | Stroble ................ A61K 31/192 514/570 |
| 2002/0187187 A1 | 12/2002 | Ohki et al. |

(Continued)

FOREIGN PATENT DOCUMENTS

| AU | 673675 B2 | 11/1996 |
| DE | 4217971 C1 | 10/1993 |

(Continued)

OTHER PUBLICATIONS

Meloxicam Summary, Committee for Veterinary Medicinal Products: Meloxicam, 1997, 7 pages.*
Abstract in English for JPH06157312, 1994.
Abstract in English of WO1999039730, 1999.
Ansel et al., "Dosage Form Design: Pharmaceutic and Formulation Considerations". Pharmaceutical Dosage Forms and Drug Delivery Systems, Seventh Edition, Lippincott Williams & Wilkins, Philadelphia, PA, 1999, pp. 66 and pp. 89.

(Continued)

*Primary Examiner* — Kyle Purdy
(74) *Attorney, Agent, or Firm* — Marc Began; Joyce L. Morrison

(57) ABSTRACT

A method of treating animals includes administering water soluble granules to an animal, where the water soluble granules include meloxicam, salt forming agent operable to form a meloxicam salt, a binder, and a carrier.

14 Claims, No Drawings

(56) References Cited

U.S. PATENT DOCUMENTS

| | | | |
|---|---|---|---|
| 2004/0037869 A1 | 2/2004 | Cleverly et al. | |
| 2004/0110747 A1* | 6/2004 | Altman | A61K 45/06 514/226.5 |
| 2004/0170687 A1 | 9/2004 | Hurd et al. | |
| 2004/0204413 A1 | 10/2004 | Faour et al. | |
| 2004/0229038 A1 | 11/2004 | Cooper et al. | |
| 2004/0234596 A1 | 11/2004 | Ohki et al. | |
| 2004/0253312 A1 | 12/2004 | Sowden et al. | |
| 2005/0147664 A1 | 7/2005 | Liversidge et al. | |
| 2005/0244491 A1 | 11/2005 | Ohki et al. | |
| 2007/0077296 A1 | 4/2007 | Folger et al. | |
| 2010/0015184 A1 | 1/2010 | Tuel | |
| 2011/0275618 A1 | 11/2011 | Folger et al. | |
| 2015/0051198 A1 | 2/2015 | Folger et al. | |
| 2017/0035885 A1 | 2/2017 | Henke et al. | |

FOREIGN PATENT DOCUMENTS

| | | |
|---|---|---|
| EP | 0002482 A1 | 6/1979 |
| EP | 0127400 A2 | 12/1984 |
| EP | 0945134 A1 | 9/1999 |
| EP | 1568369 A1 | 8/2005 |
| GB | 2455875 A | 6/2009 |
| JP | S52102416 A | 8/1977 |
| JP | S6191118 A | 5/1986 |
| JP | H06157312 A | 6/1994 |
| JP | H0912426 A | 1/1997 |
| WO | 9939730 A1 | 8/1999 |
| WO | 9949867 A1 | 10/1999 |
| WO | 9955320 A1 | 11/1999 |
| WO | WO 0241899 A1 * | 5/2002 |
| WO | 02085331 A1 | 10/2002 |
| WO | 2005002542 A2 | 1/2005 |
| WO | 2006015942 A1 | 2/2006 |
| WO | 2007039417 A1 | 4/2007 |
| WO | 2011138197 A2 | 11/2011 |

OTHER PUBLICATIONS

Ansel et al., "Pharmaceutical Dosage Forms and Drug Delivery Systems". Seventh Edition, Lippincott Williams & Wilkins, Philadelphia, PA, 1999, pp. 77-87.

Bi et al., "Evaluation of Rapidly Disintegrating Tablets Prepared by a Direct Compression Method". Drug Development and Industrial Pharmacy, vol. 25, No. 5, 1999, pp. 571-581.

International Preliminary Examination Report for PCT/EP2003/011802 dated Feb. 1, 2005.

International Search Report and Written Opinion for PCT/EP2003/011802 dated Feb. 3, 2004. [Please see International Preliminary Examination Report for translation of Written Opinion.]

Kumar et al., "Comparative Studies on Effect of Some Hydrophilic Polymers on the Dissolution Rate of a Poorly Water Soluble Drug, Meloxicam". Indian Drugs, vol. 39, No. 6, Apr. 2002, pp. 323-329.

Lieberman et al., "Tablet Formulation and Design" in Pharmaceutical Dosage Forms: Tablets, vol. 1, Second Edition, Marcel Dekker, Inc., New York, New York, 1989, pp. 105-108.

Mesh to Micron Conversion Chart, 2 pages. [Accessed at http://www.showmegold.org/news/mesh.htm on Aug. 22, 2013].

Nash et al., "A Relationship Between Screen Opening and Mesh Size for Standard Sieves"., Pharmaceutical Development and Technology, vol. 2, No. 2, 1997, pp. 185-186.

Parikh et al., Binders and Solvents, Chapter 4, Handbook of Pharmaceutical Granulation Technology, First Edition, Marcel Dekker, 1997, pp. 59-67.

Pharmaceutical Excipient Encyclopedia, Yakuji Nippo Ltd., Tokyo, 1994, pp. 2-5.

Rantanen et al., "Process Analysis of Fluidized Bed Granulation". AAPS PharmsciTech, vol. 2, No. 4, Article 21, 2001, 8 pages.

Rudnic et al., "Oral Solid Dosage Forms"., Gennaro, Editior, Remington's Pharmaceutical Sciences, 18th Edition, Mack Publishing Company, Easton, PA, 1990, pp. 1633-1645 and pp. 1654-1655.

Saha et al., "Effect of solubilizing excipients on permeation of poorly water-soluble compounds across Caco-2 cell monolayers". European Journal of Pharmaceutics and Biopharmaceutics, vol. 50, No. 3, 2000, pp. 403-411, Abstract accessed at http://cat.inist.fr/?aModele=afficheN&cpsidt=798854, accessed on Aug. 13, 2010, 3 pages.

Sciencelab.com, "Lactose, Monohydrate, Spray-Dried Powder, NF". Accessed at http://www.epoxy-paint.net/page/.S/PVAR/10419/SLL1453, Feb. 29, 2008, 2 pages.

Sharma et al., "Adsorption of Meloxican on Porous Calcium Silicate: Characterization and Tablet Formulation". AAPS PharmSciTech, vol. 6, No. 4, Article 76, 2005, pp. E618-E625.

Swamy et al., "Orodispersible tablets of meloxicam using disintegrant blends for improved efficacy"., Indian Journal of Pharmaceutical Science, vol. 69, No. 6, 2007, pp. 836-840. [Accessed at http://ijpsonline.com/article.asp?issn=0250-474X;year=2007;volume=69;issue=6;spa . . . on Jun. 16, 2013].

Vippagunta et al., "Crystalline solids". Advanced Drug Delivery Reviews, vol. 48, 2001, pp. 3-26.

* cited by examiner

WATER-SOLUBLE MELOXICAM GRANULES

CROSS REFERENCE TO RELATED APPLICATIONS

This application is a divisional of U.S. patent application Ser. No. 13/799,815, filed 13 Mar. 2013 and entitled "Water-Soluble Meloxicam Granules," which is a continuation of U.S. patent application Ser. No. 10/694,569, filed 27 Oct. 2003 and entitled "Water-Soluble Meloxicam Granules," which claims priority to U.S. Provisional Patent Application Ser. No. 60/508,184, filed 2 Oct. 2003 and entitled "Water-Soluble Meloxicam Granules," and which claims priority to German Patent Application No. DE 10250081, filed 25 Oct. 2002. Each of the aforementioned disclosures is incorporated herein by reference in its entirety.

FIELD OF THE INVENTION

The present invention relates to meloxicam granules which dissolve rapidly in water, containing meloxicam, a salt forming agent which forms the meglumine, sodium, potassium, or ammonium salt of meloxicam, binders, a sugar or sweetener, a carrier, optionally a flavoring, and optionally other excipients, processes for preparing them, and their use for treating respiratory or inflammatory complaints in mammals.

BACKGROUND OF THE INVENTION

Meloxicam (4-hydroxy-2-methyl-N-(5-methyl-2-thiazolyl)-2H-1,2-benzothiazine-3-carboxamide-1,1-dioxide) is an active substance which belongs to the group of NSAIDs (non-steroidal-antiinflammatory drugs). Meloxicam and the sodium and meglumine (N-methyl-D-glucamine) salt thereof are described in EP-A-0 002 482. EP-A-0 945 134 discloses the pH-dependent solubility characteristics of meloxicam and its salts, i.e., the sodium salt, the ammonium salt, and the meglumine salt, in aqueous solution. According to this, meloxicam is an active substance which does not dissolve readily in water. The meloxicam salts, particularly the meglumine salt, exhibit improved solubility as the pH increases between 4 and 10, as shown in Table 1 of EP-A-0 945 134.

It is known that administering medicaments to sick animals, particularly those suffering from fever, can be done particularly easily and successively through their drinking water. Administering to their food can also make it easier to give the medicament to the animal. It is known from EP-A-0 945 134 that meloxicam and meglumine cannot easily be compressed. The aim of the present invention is therefore to develop a granulated form of meloxicam which can be administered to the animals by mixing it into their drinking water or as a food supplement.

DESCRIPTION OF THE INVENTION

Surprisingly, meloxicam granules have been discovered which can easily be produced by a fluidized bed method and which, when dissolved in water, form a drinking water solution which is stable over at least 48 hours. It was also found that these granules can be added to the animals' food.

The invention therefore relates to water soluble granules containing meloxicam, a salt forming agent which forms the meglumine, sodium, potassium, or ammonium salt of meloxicam, binders, a sugar or sweetener, a carrier, optionally a flavoring, and optionally other excipients.

The meloxicam granules according to the invention have a number of advantages over existing preparations.

In sick animals, an increased uptake of drinking water can be observed when a drink containing meloxicam is given. Suitable dilution of the dissolved granules allows a variable, precise dosing of the active substance meloxicam. Because of the good solubility of the meloxicam granules according to the invention in water, the effects of meloxicam in the body of the sick animal set in very rapidly. The good flavor of the meloxicam granules also makes it possible to administer them as a food supplement. In addition, the granules according to the invention have very good flow properties, a uniform meloxicam content, they are virtually free from dust and have a narrow particle size distribution of 125 μm to 500 μm. The total solubility of the granules in water ensures optical control of a totally dissolved active substance which is only available for therapeutic use in this form when administered in drinking water. In a preferred embodiment of the invention, the salt forming agent is meglumine In another preferred embodiment of the invention, the binder may be selected from among hydroxypropylmethylcellulose, polyvinylpyrrolidone, gelatine, starch, and polyethylene glycol ether, preferably hydroxypropylmethylcellulose, polyvinylpyrrolidone, and polyethylene glycol ether, most preferably hydroxypropylmethylcellulose and polyvinylpyrrolidone.

In another preferred embodiment of the invention, the sugar or sweetener may be selected from among sodium saccharine, aspartame, and SUNETT® sweetener (acesulfame potassium, preferably sodium saccharine or aspartame. Particularly preferred according to the invention are meloxicam granules in which the flavoring is selected from among vanilla, honey flavoring, apple flavoring, and contramarum, preferably honey flavoring and apple flavoring. Also particularly preferred are meloxicam granules in which the carrier is selected from among lactose, glucose, mannitol, xylitol, sucrose, and sorbitol, preferably glucose, lactose, or sorbitol, more preferably glucose or lactose, most preferably glucose.

Particularly preferred are meloxicam granules in which the content of meloxicam is between 0.05% and 4%, preferably between 0.1% and 2%, preferably between 0.3% and 1.5%, more preferably between 0.4% and 1%, most preferably 0.6%. Also particularly preferred are meloxicam granules which contain meglumine and meloxicam in a molar ratio of about 9:8 to 12:8, preferably 10:8.

The invention further relates to process for preparing the meloxicam granules according to the invention in which the steps (a) to (c) are carried out successively:
 (a) preparing an aqueous granulating liquid containing binder, optionally a sugar or sweetener, meloxicam, meglumine, and/or a flavoring;
 (b) spraying the granulating liquid on to a carrier in a topspray fluidized bed method with an air current supplied at a constant temperature from 50° C. to 80° C., preferably 65° C.; and
 (c) a subsequent coating process with an aqueous granulating liquid by the topspray fluidized bed method containing a binder, a sugar or sweetener, and/or a flavoring.

In a preferred process according to the invention the granulating liquid is prepared by stirring and heating the components to 70° C. to 100° C., preferably about 90° C.

A particular feature of the meloxicam granules according to the invention is that they have a long term stability of 24 months or more when stored in their original package at room temperature.

A particularly preferred granulated meloxicam preparation contains meloxicam, meglumine, hydroxypropylmethylcellulose, povidone, and glucose monohydrate.

The present invention further relates to the use of meloxicam granules for preparing a pharmaceutical composition for treating pain, inflammation, fever, acute mastitis, diarrhea, lameness, problems of mobility, and respiratory complaints in animals, preferably acute mastitis, diarrhea, lameness, mobility problems, and respiratory complaints, preferably acute mastitis, diarrhea, lameness, mobility problems, and respiratory complaints, most preferably mobility problems or respiratory complaints. The treatment may be given in conjunction with antibiotic treatment.

The formulation according to the invention is suitable for treating animals, preferably mammals, particularly domestic pets or farm animals, such as pigs, horses, cattle, dogs, or cats, preferably pigs or horses.

The meloxicam granules according to the invention are preferably used in amounts corresponding to a dosage range from 0.2 to 1.0 mg of active substance per kg of bodyweight, preferably 0.4 to 0.8 mg/kg of bodyweight, preferably 0.5 to 0.7 mg/kg of bodyweight, more preferably 0.6 mg/kg of bodyweight.

It is also preferable to use the meloxicam granules according to the invention to prepare a pharmaceutical composition which can be administered both in drink and also as a feed supplement.

The formulation according to the invention may contain, as the meloxicam salt, the meglumine, sodium, potassium or ammonium salt, preferably the meloxicam meglumine salt.

The proportion of meglumine is between 0.035% and 2.8%, preferably 0.07% to 1.4%, preferably 0.21% to 1.05%, more preferably 0.28% to 0.7%, particularly about 0.42% in the meloxicam granules. The possible concentrations of sodium, potassium, and ammonium may be calculated accordingly.

The concentration of the binder may be in the range from 20 mg/g to 80 mg/g, preferably 30 mg/g to 70 mg/g, preferably 40 mg/g to 60 mg/g, most preferably 50 mg/g of granules.

The concentration of the sugar may be in the range from 50 mg/g to 150 mg/g, preferably 75 mg/g to 125 mg/g, more preferably about 100 mg/g of granules.

The concentration of the sweetener may be in the range from 1 mg/g to 10 mg/g, preferably 2 mg/g to 5 mg/g, more preferably about 3 mg/g of granules.

The concentration of the carrier may be in the range from 800 mg/g to 985 mg/g, preferably 900 mg/g to 960 mg/g, more preferably about 930 mg/g of granules.

The concentration of the flavoring may be in the range from 0.1 mg/g to 10 mg/g, preferably 0.2 mg/g to 1.0 mg/g, more preferably about 0.5 mg/g of granules.

The packaging material used for the formulation according to the invention may be any of a number of standard commercial materials for granules. These include, for example, plastic containers, e.g., made of HPPE (high pressure polyethylene), aluminum bags, or paper bags with an aluminum lining.

The meloxicam granules are produced by the top spray fluidized bed method. In this, first of all an aqueous granulating liquid solution consisting of about 50 to 70 g/kg of binder, such as PVP 25000, hydroxypropylmethylcellulose or Macrogol 6000, preferably hydroxypropylmethylcellulose, and/or about 1 to 5 g/kg of sweeteners such as SUNETT® sweetener (acesulfame potassium) or Na saccharine, preferably SUNETT® sweetener (acesulfame potassium), and/or about 0.5 to 2.5 g of flavoring, such as vanilla, honey, flavoring 203180, or contramarum, preferably honey, about 10 g to 15 g of meloxicam (peg milled) and about 7 g to 11 g of meglumine is produced with stirring by heating to about 70° C. to 100° C.

The granulating liquid is then sprayed on to a carrier such as lactose, glucose, or sorbitol, preferably glucose, by a counter flow process (top spray process). This is done, for example, using a two-component nozzle, spraying at a constant air pressure at about 50° C. to 80° C., preferably at about 65° C. The coating process may then be carried out using a second aqueous granulating liquid. In order to prepare a solution ready for use, a stock solution should be dissolved completely in water. Then the stock solution may be adjusted to the desired concentration for use by mixing with water. To increase safety in use, the granules may have water soluble color markings.

The meloxicam granules according to the invention will be illustrated by the examples that follow. The skilled person will be aware that these examples are intended solely as an illustration and should not be regarded as limiting the invention.

EXAMPLE 1

0.6% Meloxicam Granules

| Recipe: | g/100 g |
|---|---|
| Meloxicam | 0.6 |
| Meglumine | 0.42 |
| Hydroxypropylmethylcellulose | 3.00 |
| Povidone | 2.00 |
| Glucose monohydrate | 93.98 |

EXAMPLE 2

1.2% Meloxicam Granules

| Meloxicam | 1.2 |
|---|---|
| Meglumine | 0.84 |
| Hydroxypropylmethylcellulose | 3.00 |
| Collidone 25 | 2.0 |
| Glucose Monohydrate | 92.96 |

EXAMPLE 3

0.6% Meloxicam Granules

| Meloxicam | 0.6 |
|---|---|
| Meglumine | 0.42 |
| Pharmacoat 606 | 4.0 |
| Macrogol 6000 | 1.0 |
| Acesulfame K | 0.3 |
| Lactose | 93.68 |

EXAMPLE 4

0.6% Meloxicam Granules

| | |
|---|---|
| Meloxicam | 0.6 |
| Meglumine | 0.42 |
| Pharmacoat 606 | 4.75 |
| Macrogol 6000 | 0.25 |
| Acesulfame K | 0.3 |
| Liquid vanilla flavoring | 0.05 |
| Lactose | 93.63 |

Bright yellow free flowing meloxicam granules corresponding to Examples 1 to 4 may be prepared as follows:

The granules are stored for 3 months at 25° C. at a relative humidity of 60%. No significant changes were observed in terms of the active substance content, the water content (according to Karl-Fischer), the visual solubility characteristics, the pH in demineralized water, and the visual wettability. In order to determine the visual solubility characteristics, 5 g of the granules were dissolved in 100 mL of demineralized water at ambient temperature. After about 1 minute, a clear yellowish solution was obtained.

What is claimed:

1. A method of treating animals comprising administering free flowing water soluble granules to a non-human animal, the free flowing water soluble granules consisting of:
   meloxicam;
   a salt forming agent which forms the meglumine, sodium, potassium, or ammonium salt of meloxicam;
   a binder;
   a sugar or sweetener;
   a carrier; and
   optionally a flavoring agent;
   wherein 5 g of said granules dissolve in 100 mL of demineralized water in about 1 minute to form a clear solution, and the water soluble granules do not include cyclodextrin.

2. The method of claim 1, further comprising dissolving the free flowing water soluble granules in water prior to administration.

3. The method of claim 1, further comprising mixing the free flowing water soluble granules with animal feed prior to administration.

4. The method of claim 1, wherein the salt forming agent is meglumine.

5. The method of claim 1, wherein the binder is selected from hydroxypropylmethylcellulose, polyvinylpyrrolidone, gelatine, starch, or polyethylene glycol ether.

6. The method of claim 5, wherein the binder is present in an amount of 20 mg/g to 150 mg/g.

7. The method of claim 1, wherein the free flowing water soluble granules are administered in conjunction with antibiotic treatment.

8. The method of claim 1,
   wherein the one or more non-human animals are selected from the group consisting of horses, pigs, cattle, dogs, and cats, and the granules are administered to each non-human animal in a dosage such that the non-human animal receives an amount of meloxicam from 0.2 to 1.0 mg/kg bodyweight of the non-human animal.

9. The method of claim 1, wherein the meloxicam granules include meglumine, hydroxypropylmethylcellulose, povidone, and glucose monohydrate.

10. The method of claim 1, wherein the granules have a particle size distribution of 125 µm to 500 µm, and the granules are administered to the non-human animal in a dosage such that the non-human animal receives an amount of meloxicam from 0.2 to 1.0 mg/kg bodyweght of the non-human animal.

11. The method of claim 1, wherein:
   the salt forming agent is meglumine; and
   the molar ratio of meglumine and meloxicam is 9:8 to 12:8.

12. The method of claim 1, wherein the meloxicam is present in an amount of at least 0.5 mg/kg to 1.0 mg/kg bodyweight of the animal.

13. The method of claim 1, wherein the non-human animal is suffering from one or more indications selected from the group consisting of pain, inflammation, fever, acute mastitis, diarrhea, lameness, problems of mobility, and a respiratory complaint.

14. A method of treating animals comprising administering free flowing water soluble granules to a non-human animal, wherein each granule comprises:
   a carrier comprising glucose, lactose, or sorbitol;
   a first granulating composition sprayed on to the carrier so as to form a combined carrier-first granulating composition, the first granulating composition comprising meloxicam, a salt forming agent which forms the meglumine, sodium, potassium, or ammonium salt of meloxicam, a binder, and optionally a component comprising a flavoring agent and/or a sweetener; and
   a second granulating composition sprayed on to coat the combined carrier-first granulating composition, the second granulating composition comprising the binder and the component comprising the flavoring agent and/or the sweetener.

* * * * *